United States Patent [19]

Eaton et al.

[11] Patent Number: 5,137,736

[45] Date of Patent: Aug. 11, 1992

[54] PRODUCTION OF PROPIONIC ACID SALTS BY FERMENTATION OF LACTATES USING SELENOMONAS RUMINANTIUM

[75] Inventors: David C. Eaton; Alan Gabelman, both of Landenberg, Pa.

[73] Assignee: Hercules Incorporated, Wilmington, Del.

[21] Appl. No.: 803,863

[22] Filed: Dec. 9, 1991

[51] Int. Cl.⁵ .................. C12P 7/52; C12P 7/40; A23B 4/12; A23L 1/221

[52] U.S. Cl. .................................. 426/7; 426/41; 426/61; 426/650; 435/41; 435/136; 435/140; 435/141

[58] Field of Search ............... 435/141, 140, 136, 41; 426/7, 41, 61, 650

[56] References Cited

U.S. PATENT DOCUMENTS

| | | | |
|---|---|---|---|
| 1,865,146 | 6/1932 | Sherman | 435/141 |
| 1,910,130 | 5/1933 | Sherman | 435/42 |
| 4,138,498 | 2/1979 | Das | 426/61 |
| 4,676,987 | 6/1987 | Ahern et al. | 426/41 |
| 4,794,080 | 12/1988 | Mays et al. | 435/141 |

OTHER PUBLICATIONS

"Journal of Microbiol" M. J. Paynter et al vol. 61, pp. 1-7 (1970).

*Primary Examiner*—Herbert J. Lilling
*Attorney, Agent, or Firm*—Roy V. Jackson

[57] ABSTRACT

A process for preparing the sodium or calcium salt of propionic acid, comprising fermenting with the bacterium *Selenomonas ruminantium* an aqueous medium containing corn steep liquor or soy peptone, lactic acid, carbon dioxide, and sodium hydroxide, calcium carbonate, or calcium hydroxide as a neutralizing agent, the said process providing a yield in the said medium of at least 1% of the salt of propionic acid.

19 Claims, 3 Drawing Sheets

5,137,736

PRODUCTION OF PROPIONIC ACID SALTS BY FERMENTATION OF LACTATES USING SELENOMONAS RUMINANTIUM

This invention relates to a process for preparing salts of propionic acid by fermentation of lactates with the bacterium, *Selenomonas ruminatium*.

BACKGROUND OF THE INVENTION

There is a strong commercial demand for propionic acid as a source for propionic esters that are used for producing natural fruit flavors, but its use is hampered by the high cost of producing it. It is well known that when *S. ruminantium* grows on a lactic acid or lactate medium, it metabolizes the medium to $CO_2$ and a mixture of propionic, acetic, and succinic acids. See, for instance, U.S. Pat. No. 4,138,498, which is concerned with the removal of excess lactic acid in the diet of ruminants by addition to the diet of a co culture containing *S. ruminantium*. Also an extensive article by Linehan, et al.,published in 1978, disclosed essentially experimental scale data relating to the title subject, "Nutritional Requirements of *Selenomas ruminantium* for Growth On Lactate, Glycerol, or Glucose"; see *Applied and Environmental Microbiology*, Vol. 35, No. 2. The Linehan et al. studies of comparative growth rates were not concerned with processing and related yield factors that would be relevant to the commercial production of propionic, acetic, and succinic acids that can be purified for use in flavors.

Co-culture processes that may use *S. ruminantium* are disclosed in U.S. Pat. Nos. 1,910,130 and 4,794,080, but are not suitable for making propionic acids for commercial use in flavors; they have serious disadvantages, including the difficulty of maintaining stability of the co culture and avoiding contamination by other microorganisms.

The commercial value of flavors is enhanced if they can be characterized as "natural" products, that is, for instance, if they are plant or animal products or if they are made from natural starting materials by biological fermentation or enzymatic alteration. When selling kosher foods, their value is further enhanced if they are not made from meat or a dairy product, and therefore are "parve", so that only one inventory of the flavor is required. Synthetic propionic acid flavors, which are not "natural", and those made from the lactose in whey by strains of *Propionibacterium acidipropionici* (as disclosed in many U.S. Patents, such as U.S. Pat. Nos. 1,459,959, 1,865,146, and 4,676,987), which produce propionic acid, are not appropriate for commercial production of natural kosher flavoring materials.

There is therefore a need for a process for preparing propionic acid salts by fermentation of a natural starting material, that can produce kosher propionates for conversion into propionate esters for use in flavoring foods after conventional processing and purification, and in commercially economic yields, for instance, 2 to 3% propionic acid (as sodium propionate), produced by fermentation for about 72 hours, and preferably for about 48 hours.

SUMMARY OF THE INVENTION

The invention involves the anaerobic growth of *S. ruminantium* on lactic acid or glucose in a fermentation medium, preferably sterilized, which produces salts of propionic acid and other products in order to supply the energy and materials for growth. It comprises an improved process for preparing sodium propionate from sodium lactate, for instance, for conversion to propionic acid, in at least 1% and preferably 2% yield, and up to 2.4%, based on about 48 hours of fermentation of the lactate. Smaller amounts of acetate and succinate are concurrently produced.

The fermentation medium preferably contains corn steep liquor (CSL), available from Corn Products, which is also a source of part of the lactate required and gives the highest yield of product. If Corn Products' CSL lacks kosher certification, it is replaced by a CSL that has such certification, such as that available from National Starch and Chemical. Soy peptone can be substituted for the CSL in the fermentor medium (See Table 2), but is less preferred and is not a source of lactic acid.

By the process of the invention, about 5 moles of lactate are converted by *S. ruminantium* to 3 moles of propionate, 1.7 moles of acetate, 0.4 moles of succinate, and 1.7 moles of carbon dioxide.

The lactic acid is neutralized by a suitable base, preferably sodium hydroxide. If it is neutralized by calcium carbonate ($CaCO_3$) or lime ($Ca(OH)_2$) instead of NaOH, salts of calcium would predominate in the fermentation broth. (This would allow the spray dried broth to be sold as a natural calcium propionate, which is often used as a bread preservative, if the price happens to be favorable.)

Since *S. ruminantium* is a strict anaerobe, sodium sulfide or another suitable reducing agent (such as cysteine) is added to the medium in an amount of about 0.1–2.5 g/l in order to remove all but traces of $O_2$, and a yeast extract such as Tastone 154 , available from Universal Foods Corporation, Milwaukee, Wis., is preferably also added.

The fermentation can be run as a batch, semi-continuous (fed batch), or fully continuous fermentation procedure, and the medium may be sterilized either by heat or by filtration. In the latter case, which has the highest productivity rate, a mixture of lactic acid and fermentation medium is added continuously to the fermentor while the lactate-depleted (and propionate-enhanced) broth is continuously withdrawn for purification to isolate the propionic acid salt.

The semi-continuous process according to the invention (described in Examples 7 and 8) may be preferred because it allows the fermentation to be carried out with a very small inoculum, i.e., less than 1% of the final fermentor volume.

The semi-continuous process is run by initially adding 3% lactic acid, and whenever the initial lactic acid is depleted by the fermentation, adding another 2% lactic acid until the maximum yield is reached. In a variation of the semi-continuous fermentation, the fermentation vessel (fermentor) is partially filled (preferably to about 20% of the working volume of the fermentor) with growth medium, preferably containing 3% lactic acid. This starting volume is then inoculated with a culture of *S. ruminantium*. After allowing enough time for growth to occur, the fermentor is filled to capacity and the remainder of the fermentation is carried out batch-wise (although more lactic can be added later if desired).

The invention also contemplates a fermentation product mix of up to 5% lactate, carbon dioxide, sufficient $Na_2S$ or other suitable reducing agent to eliminate all but traces of oxygen, and the fermentation products propionate, acetate and succinate salts, the content of propionic acid (as sodium propionate) being at least 1%. In the preferred fermentation mix, the products propionic acid, acetic acid and succinic acid as their respective salts will be in a mole ratio of about 7.5:4.2:1.0, respectively.

*S. ruminantium* is a better selection for industrial use than the other bacteria that make propionic acid because of its rapid growth, no necessity for pH control, lack of production of $H_2$ (no safety problem), freedom from bacterial contamination since the substrate is lactic acid, lack of bacterial phage sensitivity, and greater ability to detoxify oxygen.

DETAILED DESCRIPTION OF THE INVENTION

The process uses lactic acid (d, l, or dl) in the fermentation medium, preferably 88% l- or dl-lactic acid. The yeast extract is preferably added to the medium as a source of growth factors, and vitamins such as d-biotin, p-aminobenzoic acid (PABA), choline, folic acid, inositol, niacin, pantothenic acid, pyridoxine, riboflavin, and thiamine, are preferably added to further stimulate the growth of the *S. ruminantium*. Preferably, at least d biotin and PABA are used.

Even though $CO_2$, which is required for growth, is a product of the fermentation, it is preferably added at least during early fermentation, and $Na_2CO_3$ is preferably added to act as a pH buffer and as an additional source of $CO_2$. Minerals such as sodium molybdate or selenate; ferric, manganese, zinc or copper sulfate, sodium chromate, or boric acid, are preferably added also.

According to the invention, preferably *Selenomonas ruminantium* ATCC (American Type Culture Collection, Rockville, Md.) strain numbers 27209, 19205, and 12561 can be used, as well as strain HD-4 (T. Miller, Wadsworth Center for Laboratories & Research, New York State Dept. of Health, Albany, N.Y.). Strain #27209 is most preferred.

The fermentation according to the invention can convert about 5 moles of lactate to 3 moles of propionate, 1.7 moles of acetate, 0.4 moles of succinate, and 1.7 moles of carbon dioxide. The metabolic pathway has several branches, and shows that $CO_2$ is a growth requirement for *S. ruminantium* and is also a product of the fermentation in a 1:1 ratio with acetate. Addition of two reducing agents (such as $Na_2S$ plus cysteine) does not improve growth.

For any of the possible variations of the fermentation process, the sterilization of the medium can be either by heating, or by filtration of the soluble components before addition of unfilterable medium components (such as the yeast extract and corn steep liquor), which are heat sterilized and added to the fermentor separately as a concentrated mixture. Prior to sterilization by filtration, the medium should undergo a heat treatment, preferably at about 80° C. for 30 minutes, in order to reduce the concentration of dissolved oxygen. In this case, at the start of cool down the medium is sparged with $CO_2$ by bubbling the gas through the liquid, and this sparge is maintained until the medium is transferred to the fermentor, to prevent leakage of oxygen into the medium and to saturate the medium with $CO_2$ in order to control the pH by a $CO_2$-$Na_2CO_3$ buffer system.

In order to use the process on a periodic basis, *S. ruminantium* must be stored in such a way that it can be recovered in a viable condition. Freezing is a commonly used technique to store microorganisms, but *S. ruminantium* is somewhat unstable when frozen. A special medium for storage containing glycerol and lactose enhances the stability of the frozen cells.

The formula for a preferred corn steep liquor fermentation medium is shown in Table 1, and for a soy peptone medium in Table 2. Corn steep liquor is preferably obtained as an aqueous concentrate (about 50% solids), and is used at a concentration of 0–50 g/l, but preferably is used at 5.0 g/l of final fermentor volume. Lactic acid in a grade suitable for fermentation, is preferably 88% l- or dl-lactic acid, and is added to the medium to provide a concentration of 0–5% (w/v), preferably 1–3%. The corn steep liquor typically already contains about 10% (of wet weight) lactic acid, and so larger quantities of corn steep liquor, up to about 300 g/l, can be used if the lactic acid added to the medium is reduced by the amount contributed by the corn steep liquor. Yeast extract is added to provide a concentration of 0.1–20 g/l, preferably 2.0 g/l of final fermentor volume.

If soy peptone is substituted for corn steep liquor it is used at a concentration of 0–50 g/l, preferably at 2.0 g/l, of final fermentor volume. $Na_2S$ is the preferred reducing agent for removal of oxygen because it reacts faster than cysteine. If used as $Na_2S \cdot 9H_2O$, it can be used over a wide range of 0.01–50 g/l, preferably 0.1–0.5 g/l. Biotin is used at a rate of 0.001–50 mg/l, preferably 0.1–1.0 mg/l. PABA is necessary at a concentration of about 0.001 g/l, but more can be used. The addition of $Na_2CO_3$ can be omitted if the required $CO_2$ is otherwise available for growth, such as by a slow sparging of $CO_2$ through the medium. After initial growth (or immediately if a heavy inoculum is used), $CO_2$ addition is preferable, but no longer necessary since $CO_2$ is a product of growth.

The fermentation is preferably run with sterilized equipment and media. The process can also be run less preferably with only the heat treatment of the medium (to hydrolyze the lactides and to remove the $O_2$), because it is resistant to contamination.

For a batch fermentation, a complete fermentation medium (Table 1 or 2) is prepared in a fermentor equipped with agitation and temperature control. Alternatively, the vitamins d-biotin and p-aminobenzoic acid can be prepared separately as an aqueous concentrate, and added after sterilization through a sterile filter. Sterile resazurin is preferably added to serve as a redox indicator. Enough medium is prepared to fill the fermentor to about 100% of its total working volume. The yeast extract is used at a concentration of 0–50 g/l, but preferably is used at 2.0 g/l of final fermentor volume. Corn steep liquor is used at a concentration of 0.1–20 g/l, but preferably 5.0 g/l of final fermentor volume. The fermentor with the medium is sterilized (at 121° C. for 30 minutes).

If the medium is to be sterilized by filtration, the components that are not filter-sterilizable, namely yeast extract (such as Tastone 154) and corn steep liquor, in amounts based on final fermentor volume, are combined with enough water to form a pumpable slurry (typically 100–120% of the combined weight of the yeast extract and corn steep liquor) and placed into a container suitable for heat sterilization. The pH is then adjusted to approximately 7 with a suitable base such as sodium hydroxide. The container is purged with inert gas (e.g., $N_2$ or $CO_2$), and sterilized (30 minutes at 121° C.). The pH of the filter sterilized portion of the medium is adjusted to about 7 with a suitable base such as sodium hydroxide, then 4 g/l of sodium carbonate are added, which increases the pH to about 10. $CO_2$ is sparged through the medium until the pH drops to about 7. The temperature is then increased to 50°-100° C., but preferably 82° C., and held there for 30 minutes, in order to reduce the dissolved oxygen concentration and hydrolyze some or all of the lactides present in the 88% lactic acid. The medium is cooled and held under an inert atmosphere (e.g., $N_2$ or $CO_2$) until transferred to the production fermentor. The production fermentor is sterilized (121° C. for 30 minutes), and immediately afterward a $CO_2$ purge is begun at a rate of 1.5-60 cc/liter/min. The $CO_2$ sparge is preferably maintained throughout the fermentation, or less preferably can be turned off after inoculation. The heat-treated starting medium is then sterilized by filtration into the production fermentor, and the heat sterilized ingredients are added.

Immediately before inoculation, $Na_2S \cdot 9H_2O$ at a preferable level of 0.5 g/l is added to remove any remaining oxygen. It can be prepared as a 15% solution in water and is either autoclaved, then added aseptically to the fermentor, or added directly through a sterilizing filter. Afterward the fermentor is inoculated with preferably 3-5% (v/v) of a 12-48 hour, but preferably an 18-36 hour culture of S. ruminantium, and the temperature is controlled at 25°-45° C., but preferably 39° C. Gentle agitation is used, but the rate can vary widely. Control of pH is not necessary (unless glucose is the substrate), since there is little pH change resulting from the metabolism of sodium lactate. Results, typically 36-48 hours after inoculation, are approximately as follows: lactic acid, <1 g/l; acetic acid, 6-8 g/l; propionic acid, 13-17 g/l; succinic acid, 2-4 g/l.

For a semi-continuous process, with the medium heat-sterilized, the fermentation medium (Table 1 or 2) is prepared in a fermentor equipped with agitation and temperature control. Alternatively, the vitamins d biotin and p-aminobenzoic acid can be prepared separately as an aqueous concentrate, and added after sterilization through a sterile filter. The blue dyestuff resazurin may be added, after sterilization, to serve as a redox indicator. Enough medium is prepared to fill the fermentor to about 20% of its total working volume. The fermentor is sterilized in place (at 121° C. for 30 minutes), or sterilized in the autoclave (at 121° C. for 45 minutes). After sterilization, a slow sparge of $CO_2$ is begun through a sterilizing filter, at the preferable rate of 1.5-60 cc/liter/min. The $CO_2$ sparge is preferably maintained throughout the fermentation, or less preferably can be turned off after inoculation. Immediately before inoculation, $Na_2S \cdot 9H_2O$ at a preferable level of 0.5 g/l is added to remove any remaining oxygen. It is prepared preferably as a 15% solution in water and is either autoclaved, then added to the fermentor using sterile technique, or added directly through a sterile filter. Afterward the fermentor is inoculated with 0.1-50% (v/v), but preferably 3-5% (v/v) of an 18-36 hour culture of S. ruminantium, and the temperature is controlled at 25°-46° C., but preferably 39° C. Gentle agitation is used, but the rate can vary widely. Control of pH is not necessary (unless glucose is the substrate) since there is little pH change resulting from the metabolism of sodium lactate.

In a separate fermentor, medium is prepared according to the same procedure used to prepare the starting volume, and is held under an inert gas (e.g., $CO_2$ or $N_2$) atmosphere, preferably at 39° C. This medium is added to the fermentor in order to prolong metabolism (and to thereby increase the propionic acid concentration), and to increase the volume to approximately 100% of the fermentor working volume. Suitable criteria for the start of transfer of this sterile medium to the inoculated fermentor are absorbance, concentrations of propionic acid, acetic acid, and lactic acid, or simply time since inoculation. Good results are obtained when the transfer is begun at an absorbance of 6. This typically occurs twelve hours after inoculation, when lactic, acetic, propionic, and succinic acid concentrations are typically 14, 4, 8, and 1 g/l respectively. Shortly before the start of the transfer of the feed medium to the fermentor, $Na_2S$ (preferably 0.5 g/l of $Na_2S \cdot 9H_2O$ prepared as a 15% solution in water) is either heat sterilized then added to the sterile medium aseptically, or added through a sterilizing filter. The addition of feed medium is made at a steady rate for a period of up to 48 hours, but preferably over a 4-5 hour period and at a rate of about 2 1/l-h.

Sodium lactate solution is prepared by dilution (in water) of an amount of 88% lactic acid, preferably equal to 1.5-2.5% by weight of the final fermentor volume, followed by adjustment of the pH to 7 with a base such as sodium hydroxide. The solution is purged with inert gas (e.g., $CO_2$ or $N_2$), then sterilized. If sterilization is done in place, upon cooling the vacuum should be broken with inert gas, and the sterile sodium lactate solution should be maintained under an inert gas atmosphere until transferred to the fermentor.

A suitable criterion for transfer of the sterile sodium lactate to the fermentor is the lactic acid content of the fermentor, which should be 4 g/l or lower for best results. Corresponding concentrations of acetic, propionic, and succinic acids are typically 5, 12, and 0.5-2 g/l respectively at this time. Typically about 27 hours have elapsed since inoculation when these concentrations are reached. At this point, the sterile sodium lactate solution is aseptically added, and the fermentation is allowed to continue.

Results, typically 55-65 hours after inoculation, are approximately as follows: lactic acid, <0.1 g/l; acetic acid, 9 g/l; propionic acid, 20-21 g/l; succinic acid, 4-5 g/l. At this point an additional 0-1% of lactic acid can be added, but preferably 0.3-0.5% (w/v) of 88% lactic acid, prepared as a sterile sodium lactate solution in the manner described above. Alternately, a sterile solution of sodium lactate is prepared by diluting 88% lactic acid with an equal weight of water, adjusting the pH to neutrality with base, purging with inert gas (e.g., $N_2$ or $CO_2$), and sterilizing. The lactate solution is then added to the fermentor, preferably at a rate of 1.0 g/l-h. The addition continues until the propionic acid concentration stops increasing, and/or the lactic acid concentration increases markedly. Final results are typically as follows: lactic acid, <0.1 g/l; acetic acid, 10 g/l; propionic acid, 22-23 g/l; succinic acid, 4-5 g/l.

If the medium is to be sterilized by filtration, the medium components that are not filter sterilizable must be heat sterilized. The Tastone 154 yeast extract (preferably 2.0 g/l of final fermentor volume) and corn steep liquor (preferably 5.0 g/l of final fermentor volume), are combined with enough water to form a pumpable slurry (typically 100-120% of the combined weight of the yeast extract and corn steep liquor) and placed into a container suitable for heat sterilization. The pH is then adjusted to approximately 7 with a suitable base such as sodium hydroxide. The container is purged with inert gas (e.g., $N_2$ or $CO_2$, and sterilized (30 minutes at 121° C.).

The rest of the medium is soluble and can be filter sterilized. This is composed of 34.1 g/l lactic acid (assuming 88% concentration grade), 0.04 g/l $MgSO_4 \cdot H_2O$, 0.24 g/l ammonium sulfate, 0.05 g/l $CaCl_2 \cdot 2H_2O$, 0.001 g/l d-biotin, and 0.0001 g/l p-aminobenzoic acid. Alternatively, the vitamins d-biotin and p-aminobenzoic acid can be prepared separately as an aqueous concentrate, and added directly to the sterilized fermentor through a sterilizing filter. Another variation is that all medium components except lactic acid can be included in the yeast extract/corn steep liquor concentrate described above. After the medium is prepared, enough is added to fill the production fermentor to about 20% of its total working volume. The pH is adjusted to about 7 with a base such as sodium hydroxide, then 4 g/l of sodium carbonate are added, which increases the pH to about 10. $CO_2$ is sparged through the medium until the pH drops to about 7, and the temperature of the fermentor contents is then increased to 60°–100° C., but preferably 82° C., and held there for 30 minutes, in order to reduce the dissolved oxygen concentration and hydrolyze some or all of the lactides present in the lactic acid. The medium is cooled and held under an inert atmosphere (e.g., $N_2$ or $CO_2$) until transferred to the production fermentor. The production fermentor is sterilized at 121° C. for 30 minutes. Immediately afterward a $CO_2$ purge is begun at a rate of 1–60 cc/liter/min (introduced through a sterilizing filter). The $CO_2$ sparge is preferably maintained throughout the fermentation, or less preferably can be turned off after inoculation. The heat-treated starting medium is then sterilized by filtration into the production fermentor.

One fifth of the final yeast extract/corn steep liquor concentrate is aseptically added at this time to the fermentor.

If not included in the medium earlier, the vitamins are prepared as an aqueous concentrate and added through a sterile filter. One ml/liter of sterile 0.1% resazurin (in water) may be added if desired as a redox indicator. 0.5 g/l of $Na_2S \cdot 9H_2O$ (as a 15% solution in water) is either heat sterilized then added to the fermentor, or added through a sterilizing filter. Shortly afterward, the fermentor is inoculated preferably at 3–5% (v/v) with a 12–36 hour culture of S. ruminantium. The temperature is controlled preferably at 39° C., and gentle agitation is maintained. Enough medium to fill the production fermentor to 100% of its working volume is then prepared in the same manner as described above. The medium is then held under an inert atmosphere with gentle agitation, preferably at the fermentation temperature. Transfer of the sterile medium to the production fermentor begins when the fermentation has progressed to a suitable point. Good results are obtained if the transfer begins when absorbance (600 nm) is about 4.0 or higher. This typically occurs after 12–18 hours, at which time lactic, acetic, propionic, and succinic acid concentrations are typically 11, 3, 7, and 1 g/l respectively. Transfer to the production fermentor continues for 4–5 hours at a steady rate.

Sodium lactate solution is prepared by dilution (in water) of an amount of lactic acid equal to about 2.3% by weight of the final fermentor volume, followed by adjustment of the pH to 7 with a base such as sodium hydroxide. The solution is purged with inert gas (e.g., $N_2$ or $CO_2$), then sterilized. If sterilization (30–45 minutes at 121° C.) is done in place, upon cooling the vacuum is broken with an inert gas, and the sterile sodium lactate solution is maintained under this atmosphere until transferred to the fermentor. Good results are obtained when the sodium lactate solution is added to the production fermentor when the lactate level in the latter is nearly depleted. This typically occurs about 30 hours after inoculation, at which time acetic, propionic, and succinic acid concentrations are typically 4, 9, and 2 g/l respectively. The lactate level is again nearly depleted after typically about 55 hours after inoculation. At this time acetic, propionic, and succinic acid concentrations are typically 8–9, 18–19, and 5–6 g/l respectively. If a higher yield of these acids is desired, an additional 0.3–0.5% by weight of sterile sodium lactate solution (prepared as described above) is added. Best results are obtained when the solution is fed to the fermentor at a rate of about 1 g/l-hr. Feeding continues until the lactic acid concentration begins to increase markedly, which typically occurs about 80–85 hours after inoculation. Typical final results are: acetic acid, 10 g/l; propionic acid, 22 g/l; succinic acid, 6–7 g/l.

For the continuous fermentation procedure, CSL medium (Table 1) is prepared, but with 34.1 g/l of l-lactic acid, 0.1 mg/l PABA and 1.0 mg/l biotin. The fermentor is sterilized, and upon cooldown, vacuum is broken by introduction of a $CO_2$ sparge (through a sterilizing filter) which is maintained at a rate of 1–60 cc/l-min throughout the remainder of the fermentation. Shortly before inoculation, 3.3 ml/l of a sterile 15% aqueous solution of $Na_2S \cdot 9H_2O$ is added. Afterward the fermentor is inoculated, preferably with 3–5% by volume of a 12–36 hour culture of S. ruminantium. The temperature is maintained above the ambient level, preferably at 39° C., with gentle agitation.

In a separate larger vessel equipped with agitation, the same medium is prepared and sterilized as described above. The amount of lactic acid may be varied, if desired (in order to increase the concentration in the feed vessel up to a maximum of 5%). This medium serves as the feed reservoir for the continuous fermentation, and is held under inert gas (e.g., $N_2$ or $CO_2$) sparge, with gentle agitation, and preferably at the fermentation temperature. Good results are obtained if feeding begins when the lactic acid concentration in the fermentor drops to <10 g/l, but preferably <4 g/l. Continuous feeding is begun at a steady rate with appropriate spent broth removal to maintain a constant level. Good results are obtained at a dilution rate of 0.05/h, but other dilution rates can also be used. When the fermentation is operated in this manner, a liquid stream containing high concentrations of propionate, acetate, and succinate salts is continuously produced.

THEORY OF THE INVENTION

S. ruminantium grows anaerobically on lactic acid and metabolizes it to propionic acid and other products in order to derive energy for growth. All but trace levels of oxygen ($O_2$) are toxic to the organism and will prevent growth. Thus the usual growth environment for the organism is highly reduced. But because $O_2$ is not normally available in this environment for oxidation reduction reactions, the organism must balance the redox state of the feed (lactic acid) with that of the products. In this case redox can be considered to be the ratio of hydrogen atoms (H) to oxygen atoms (O). Each molecule of lactic acid is metabolized by the organism to one of propionic acid plus one of $H_2O$, but alternatively it can also be metabolized to one of acetic acid plus one of $CO_2$. However, lactic acid ($C_3H_6O_3$) has a H:O ratio of 6/3 (=2) and this same ratio must be maintained in the products produced by metabolism.

Propionic acid ($C_3H_6O_2$) plus $H_2O$ has a H:O ratio of 8/3 (one $H_2O$ is always made for every one propionic acid). However, the product mixture of acetic acid ($C_2H_4O_2$) plus $CO_2$ minus $H_2O$ (one $CO_2$ is always made and one $H_2O$ consumed for every acetic acid formed) has a H:O ratio of 2/3. That is, propionic acid (plus $H_2O$) has a higher H:O ratio than lactic acid whereas the acetic acid plus $CO_2$ product mixture has a lower H:O ratio than lactic acid. Thus, in order to maintain a redox balance in an anaerobic environment (and have a product redox ratio of 2), 2 propionic acid molecules (plus two of $H_2O$) must be made for every one of acetic acid (plus one $CO_2$ minus one $H_2O$). This results in the desired H:O ratio of 2 (18/9=2). The equation for metabolism of lactic acid in the absence of $O_2$ is thus:

$$3 C_3H_6O_3 \longrightarrow 2 C_3H_6O_2 + C_2H_4O_2 + CO_2 + H_2O$$

In a strictly controlled anaerobic environment with excess reducing agent such as $Na_2S$, these results are obtained. However our experimental results show that if some $O_2$ is present (but of course not enough to prevent growth), then less propionic acid is produced with a concomitant increase in acetic acid. Theoretically this can be explained if $O_2$ is used by the organism to balance the redox state of the products. The equation for metabolism of lactic acid in that case becomes:

$$3 C_3H_6O_3 + 3 O_2 \longrightarrow 3 C_2H_4O_2 + 3 CO_2 + 3 H_2O$$

TABLE 1
CSL FERMENTOR MEDIUM

| | Amount (Per liter) |
|---|---|
| l-lactic acid heat stable (88%) | 57.1 g/l (3% + 2% = 5% total) |
| Corn steep liquor (50% solids) | 5.0 g |
| Tastone TM 154 | 2.0 g |
| NaOH | 11.5 g |
| $Na_2S \cdot 9H_2O$ | 0.5 g |
| $(NH_4)_2SO_4$ | 0.25 g |
| $CaCl_2 \cdot 2H_2O$ | 0.07 g |
| $MgSO_4 \cdot 7H_2O$ | 0.04 g |
| Biotin | 0.1 mg |
| PABA | 0.01 mg |

Mix (pH should be about 7.5), then add 4.0 $Na_2CO_3$ and sparge with $CO_2$ until pH 7.

TABLE 2
SOY PEPTONE FERMENTOR MEDIUM

| | Amount (Per liter) |
|---|---|
| l-lactic acid heat stable (88%) | 57.1 g/l (3% + 2% = 5% total) |
| Soy peptone (kosher) | 5.0 g |
| Tastone 154 | 2.0 g |
| NaOH | 11.5 g |
| Cysteine | 0.5 g |
| $(NH_4)_2SO_4$ | 0.25 g |
| $CaCl_2 \cdot 2H_2O$ | 0.07 g |
| $MgSO_4 \cdot 7H_2O$ | 0.04 g |
| Biotin | 0.1 mg |
| PABA | 0.01 mg |
| Trace minerals* | 11.0 ml |

The above solution has pH 7.5, prior to adding $Na_2CO_3$, and before sparging with $CO_2$ until pH 7 is obtained.

TABLE 3
COMPARISON OF CORN STEEP LIQUORS

| Additions | CSL[a] | CSL Type | $A_{600}$[f] | % Propionate |
|---|---|---|---|---|
| none | Corn Pro[b] | 50% solids | 1.00 ± 0.01 | 1.30 |
| none | Roq[c] | spray dried | 0.58 ± 0.04 | 1.27 |
| none | Nat St[d] | 50% solids | 0.96 ± 0.04 | 1.30 |
| minerals[e] | Corn Pro[b] | 50% solids | 1.09 ± .01 | 1.28 |
| minerals[e] | Roq[c] | spray dried | 0.66 ± 0.02 | 1.19 |
| minerals[e] | Nat St[d] | 50% solids | 0.95 ± 0.03 | 1.30 |

[a]CSL = corn steep liquor added at rate equivalent to 2.5 g of solids per l.
[b]Corn Pro = Corn Products, Englewood Cliffs, NJ.
[c]Roq = Roquette Corp. Gurnee, IL.
[d]Nat St = National Starch and Chemical, Indianapolis, IN.
[e]minerals = 11.0 ml/l of (g per liter) citric acid 5.5, $Na_2MoO_4 \cdot 2H_2O$ 0.025, $FeSO_4 \cdot H_2O$ 0.95, $CuSO_4 \cdot 5H_2O$ 0.05, $Na_2SeO_3$ 0.001, $ZnSO_4 \cdot 7H_2O$ 0.39, $MnSO_4 \cdot H_2O$ 0.08, $Na_2CrO_4 \cdot 4H_2O$ 0.005, $H_3BO_3$ 0.09.
[f]Results are expressed as change in $A_{600}$ over 24 hours as measured in Spec 21 - this is a measure of growth.
± Indicates 1 standard deviation.

TABLE 4
GROWTH OF SELENOMONAS RUMINANTIUM AFTER FROZEN STORAGE

| Condition[a] | 1 week frozen 30h $A_{600}$ | 11 week frozen 28h $A_{600}$ | 28 week frozen 25h $A_{600}$ |
|---|---|---|---|
| $H_2O$ (control) | .07 | .10 | .14 |
| 10% lactose | .04 | .04 | .06 |
| 10% glycerol | .14 | .03 | .10 |
| 5% whey[b] | .29 | .16 | .38 |
| 4% skim milk[c] | .00 | .01 | .00 |
| 4% skim milk[c] + 10% glycerol | .00 | .01 | .00 |
| 10% glycerol + 10% lactose | .28 | .31 | .38 |
| 10% glycerol + 5% whey[b] | .32 | .16 | .37 |
| 5% DMSO | .20 | .12 | .12 |

[a]Selenomonas ruminantium was grown (18 vials × 3 phase experiment = 54 vials) at 39° C in usual lactate based medium. With the exception of the skim milk medium the additions were made into the vials after growth and immediately before freezing at −70° C. At the indicated times, duplicate frozen vials were selected and thawed and each was used to inoculate 3 vials of our normal growth medium to check for viability. Results are the change (increase) in average growth (absorbance at 600 nm in the Spec 20 of whole vial) of these 6 vials at the indicated incubation times (at 39° C.)
[b]Kraft spray dried Krafen Kosher sweet whey.
[c]Difco dehydrated skim milk.
± Indicates 1 standard deviation - some variability is normal, but a high number implies that some of the vials in a condition did not grow.

TABLE 5
EFFECT OF STERILIZATION CONDITIONS ON THE FERMENATION MEDIUM

Conditions
A = Autoclave 30 min (pH 7)
B = Autoclave 30 min (pH 7); cool; again Autoclave 30 min
C = Autoclave 30 min pH 2.4; adjust pH, add cysteine and $Na_2CO_3$, sparge with $CO_2$; again Autoclave 30 min
D = Condition A + filter sterilized thiamine & biotin
E = Condition B + filter sterilized thiamine & biotin
F = Condition C + filter sterilized thiamine & biotin

| Condition | $A_{600}$* 19h | $A_{600}$* 43h | Propionate 19h | Propionate 43h |
|---|---|---|---|---|
| A | 3.3 ± .9 | 3.0 ± .4 | .84 | 1.23 |
| B | 3.7 ± .1 | 2.9 ± .1 | 1.09 | 1.25 |
| C | 1.0 ± .5 | 3.9 ± .7 | .29 | 1.26 |
| D | 3.2 ± .0 | 3.3 ± .1 | .80 | 1.00 |
| E | 3.4 ± .6 | 3.3 ± .0 | .70 | 1.29 |
| F | .6 ± .6 | 4.0 ± .1 | .32 | 1.29 |

*Results are average of 2-100 ml serum vials measured on a Gilford spectrophotometer and calculated from an appropriate dilution of the cell suspension (0.0-0.5 $A_{600}$).

EXAMPLE 1

Lactate Fed Fermentation With Cysteine to Form Proprionate and Acetate

A seven liter fermentor is filled with 4 liters of medium (Table 1), and heat sterilized in place. Cysteine (0.5 g/l) is added to remove oxygen, and the fermentation vessel is slowly sparged with $CO_2$ to maintain anaerobic conditions. The fermentation is inoculated with 120 ml of a culture of S. ruminantium grown for 12 hours at 39° C. in stoppered serum bottles in the medium of Table 1. After 29 hours, incubating at 39° the lactate has declined from the initial 3% lactate to about 1%. Then an additional 1.5% lactic acid (as sodium lactate) is added. This procedure resulted in lactate never exceeding 3%. After 86 hours of fermentation all lactate is consumed, and the concentrations of propionate and acetate are 2.3% and 1.2% respectively.

EXAMPLE 2

Lactate Fed Fermentation With Na2S

Figure 1:
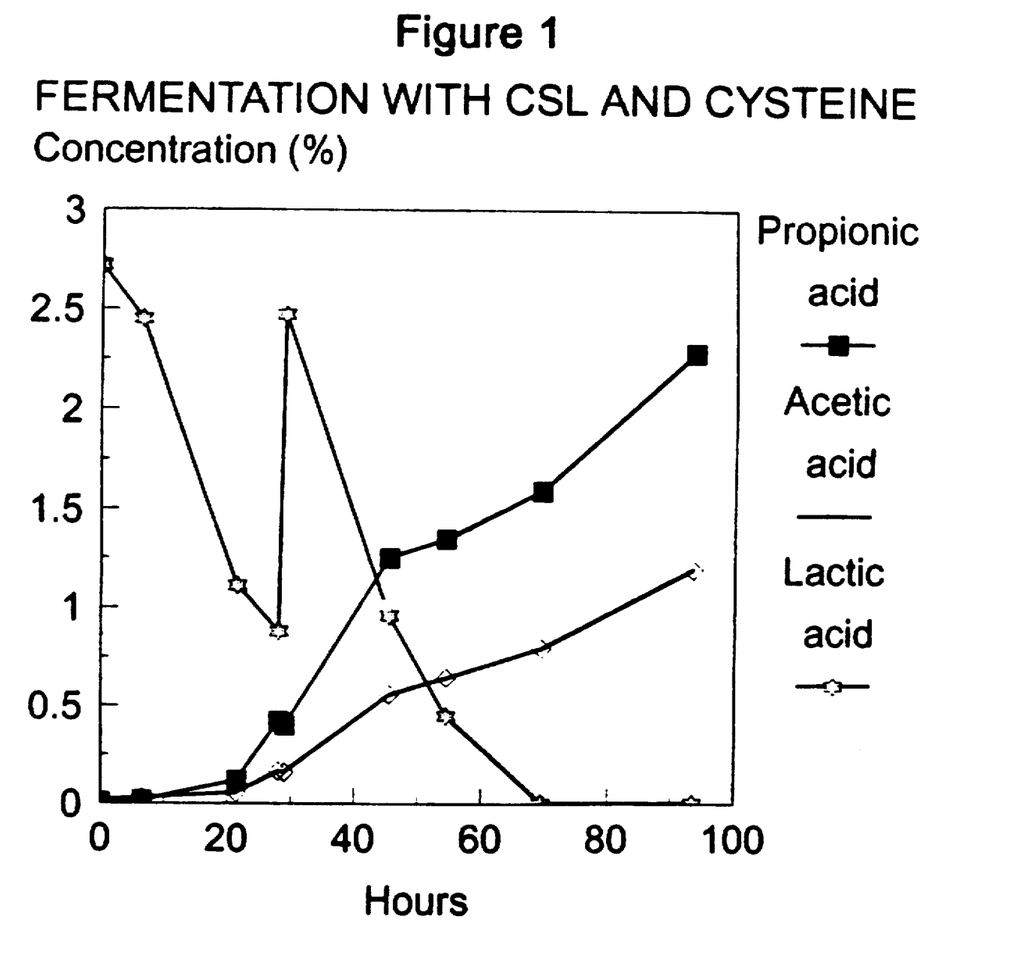
Figure 2:
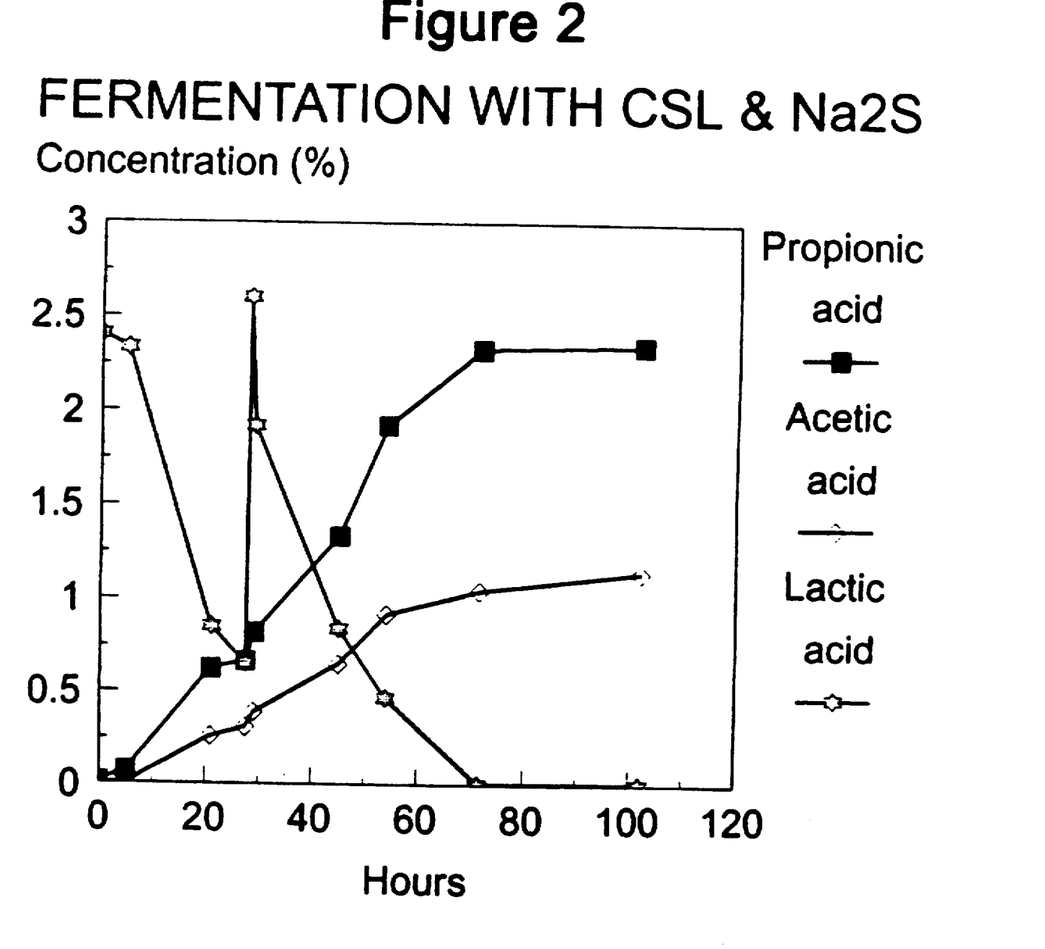
Figure 3:
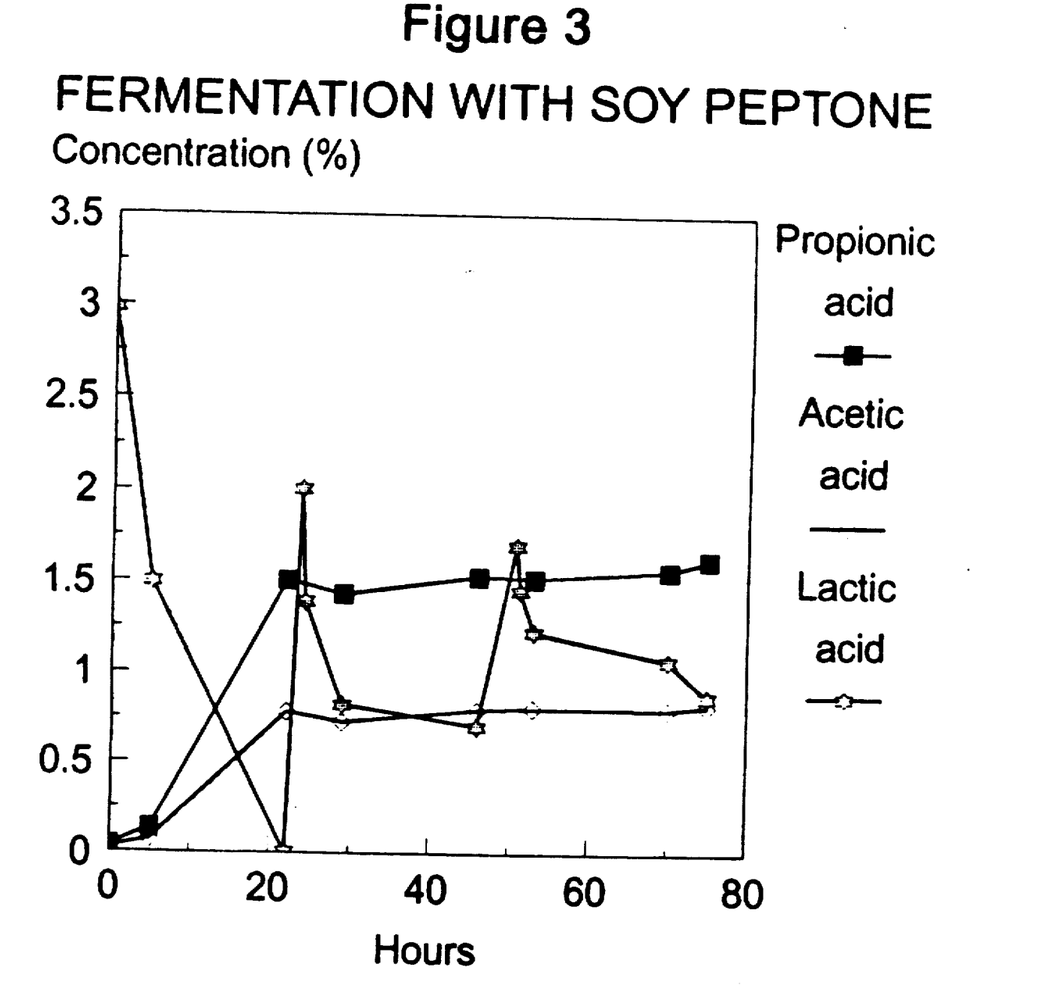

The procedure of Example 1 is followed except that $Na_2S \cdot 9H_2O$ is substituted for cysteine in the fermentation medium as the reducing agent. Lactic acid declines to 0.6% after 29 hours and then an additional 2% lactic acid is added (as sodium lactate). A total of 2.3% propionic acid is made in 72 hours. 1.0% acetate is also made. Examples 1 and 2 demonstrate that the use of $Na_2S$ as the reducing agent as shown in FIG. 2 increases the fermentation rate over that found when cysteine is used as shown in FIG. 1.

EXAMPLE 3

Frozen Storage of Stock Cultures

Cultures of S. ruminantium are initially grown in serum vials at 39° C. in the CSL based medium of Table 1, then the various other ingredients are added. With the exception of the skim milk medium, the additions are made to the vials after growth and immediately before freezing at −70° C. At various times, selected vials are thawed and each is used to inoculate 3 vials of the normal growth medium (Table 1) to check for viability. Growth is measured by increase in absorbance at 600 nm. Only three media allowed rapid growth and recovery at all three time periods with consistent growth in all vials by 25-30 hours of incubation as shown in Table 4. These three media were supplemented with either whey, glycerol and lactose or with glycerol and whey. Of the three conditions, glycerol and lactose is clearly superior as indicated consistently by the highest final growth. The use of glycerol and lactose has the additional advantage of producing a medium with a relatively clear initial appearance, which makes measurement of growth easier and more reliable.

EXAMPLE 4

Soy Peptone (5 g/l) Medium Fermentation

A 100 ml fermentation was attempted with the medium (Table 2) containing soy peptone (5 g/l ) as a replacement for CSL. The soy peptone used was Marcor Type D, which is available as a kosher certified grade. The medium also had 0.5 ml/l of Mazu DF245-59A antifoam (Mazer Chemicals, Folcroft, Pa.) to control foaming during the heat sterilization step. The vitamins were filter sterilized and added separately. The fermentation was initiated by the addition of an inoculum of *S. ruminantium* grown in 2 100-ml serum vials (about 120 ml total or 3% of the final volume). A total of 1.18% propionic acid is made in 48 hours. At this stage in the fermentation the results were almost as good as could be expected with CSL in the medium. The initial 3% lactic acid had declined to zero by 48 hours fermentation, and a further 2% lactic acid feed was added (as sodium lactate). Propionic acid then increased further to 1.34% after 72 hours, at which time the fermentation had essentially stopped. Approximately 1% lactic acid remained unused at this time. Typically, in the CSL medium, approximately 2-2.4% propionic acid is made in 72 hours incubation, with all lactic acid consumed. These results show that although soy peptone in the medium is almost as good as CSL for the first 48 hours, CSL is clearly superior for the longer-incubation higher-yield fed batch fermentation.

EXAMPLE 5

Soy Peptone (5 g/l ) Medium Fermentation With a Soy Peptone And Lactic Acid Feed The fermentation in Example 4, using soy peptone (Table 2), was repeated at a larger scale. The fermentation showed excellent propionic acid production, with accumulation of 1.5% propionic acid by 22 hours incubation (FIG. 3). By this time lactic acid had declined to 0, and an additional 2% lactic acid (as sodium lactate) was added, along with 3 g/l of soy peptone to avoid nutritional limitation. By 70 hours incubation the lactic acid had declined to 0.7%; an additional 1% lactic acid and an additional 1.5 g/l of soy peptone were then added. Despite excellent utilization of the lactic acid, only an additional 0.1% propionic acid was produced in an additional 51 hours of incubation, for a total of 1.6%. The combined feed of soy peptone and lactate thus does not increase the propionate yield in a soy peptone containing medium.

EXAMPLE 6

Heat Sterilization of Medium Components

Both CSL and yeast extract are only partially soluble, and thus require the use of heat sterilization rather than filter sterilization. If the medium could be heat sterilized at acidic pH there would be less scale build up on heat exchanger surfaces. However, some of the medium components, especially the vitamins and yeast extract, could lose nutritional value if heated at an acidic pH. In order to determine if nutritional loss is a difficulty, an experiment was set up to compare the medium (Table 1) after various heat treatments: A) neutral pH heat sterilization, B) double length (60 min vs. 30 min) neutral pH heat sterilization, C) acidic pH sterilization (30 min pH 2.4, followed by 30 min pH 7), D) neutral pH heat sterilization with filter sterilized vitamins, E) double length (60 min) neutral pH heat sterilization with filter sterilized vitamins, and F) acidic pH sterilization with filter sterilized vitamins. Each medium was placed into duplicate 6 ml serum bottles and sterilized as described above. The bottles were inoculated from an overnight culture of *S. ruminantium*. The results (Table 5) show that heat sterilization (even double length heating) at neutral pH does not harm the medium. However, heat sterilization at acidic pH greatly slows both growth and propionate production, although final yields by about two days are the same as with the control (condition A). Heat treatment at acidic pH does not cause its effect by destroying biotin or PABA since there is no benefit from the addition of filter sterilized vitamins. These results indicate that heat sterilization of the entire medium at neutral pH is acceptable while heat sterilization at acidic pH causes damage to the medium that the addition of vitamins does not repair.

EXAMPLE 7

Fed-batch Fermentation 2.5 liters of CSL medium (Table 1) were prepared in a 14 liter glass fermentor, but with 34.1 g/l of 1-lactic acid (88% aqueous solution, USP heat stable; Purac, Inc., Arlington Heights, Ill.), 2.0 g/l CSL (CPC International, Englewood Cliffs, N.J.), 0.1 mg/l PABA and 1.0 mg/l biotin. After sterilization of the fermentor in the autoclave at 121° C. for 45 minutes, a continuous slow sparge of the sterile medium with 150 cc/min of $CO_2$ (introduced through a sterile glass wool filter) was begun to prevent introduction of $O_2$. PABA and biotin were prepared as a concentrate in deionized water (biotin: 150 mg/l; p-aminobenzoic acid: 15 mg/l ), and 16.7 ml of this concentrate were then injected into the fermentor medium through a sterile 0.45 μm syringe filter. An 8.3 ml amount of a 15% solution of $Na_2S \cdot 9H_2O$ was injected through a sterile 0.45 μm syringe filter to eliminate all but traces of $O_2$.

Meanwhile 13 liters of the same medium were prepared for introduction to the above fermentor (as a feed stage of fermentation). The medium was sterilized in place for 30 minutes at 121° C., and upon cooling, vacuum was broken with a sparge of 150 cc/min of $CO_2$, which was maintained until the contents were transferred to the inoculated fermentor as described below. Temperature was maintained at 39° C., pressure at 0.1 bar gauge, and agitation at 300 RPM. Immediately before use, 86.7 ml of vitamin concentrate (prepared as above) and 43.3 ml of a 15% aqueous solution of $Na_2S \cdot 9H_2O$ were added to the 13 liters of medium through separate sterile 0.45 μm filters.

An aqueous sodium lactate concentrate was prepared as follows. 284 grams of 88% 1-lactic acid were diluted with an equal weight of deionized water in a 750-ml thick-wall glass bottle. The pH was adjusted from 1.2 to 7.0 with 107.4 g of sodium hydroxide pellets, then the solution was sparged with nitrogen for 20 minutes. The bottle was then quickly sealed (using a butyl rubber septum, steel cap, and crimping tool) to prevent leakage of oxygen into the bottle. The bottle was then autoclaved at 121° C. for 30 minutes.

The fermentor was inoculated by addition of 100 ml of a 24 hour culture of *S. ruminantium*. Temperature was controlled at 39° C., agitation at 100 RPM, and $CO_2$ sparge at 150 cc/min. Pressure was atmospheric. Twelve hours after inoculation, absorbance (600 nm) was 6.1, and 1-lactic, total lactic, acetic, propionic, and succinic acid concentrations were 7.1, 13, 3.5, 8.2, and 0.6 g/l respectively. Succinic and total lactic acids were determined by HPLC, propionic and acetic by GC, and 1-lactic by the Model 27 Analyzer (Yellow Springs Instrument Company, Inc., Yellow Springs, Ohio). At this point transfer of the feed medium (see above) to the inoculated fermentor was begun at a steady rate using a peristaltic pump and sterile tubing. The transfer was stopped after five hours, when the volume in the inoculated fermentor reached 12 liters. 28 hours after inoculation, 1-lactic, total lactic, acetic, propionic, and succinic acid concentrations were 2.0, 4.0, 4.8, 11.7,and 2.0 g/l respectively. In order to prevent exhaustion of the lactic acid (and cessation of fermentation), 45 minutes later the sterile sodium lactate solution (prepared above) was transferred to the fermentor, and the fermentation was allowed to continue. 55 hours after inoculation, 1-lactic, total lactic, acetic, propionic, and succinic acid concentrations were 0.06, 0.2, 9.1, 20.7, and 4 g/l respectively. One hour later, a sterile aqueous sodium lactate solution (prepared as described above using 60 grams of 88% 1-lactic acid) was transferred to the fermentor, and the fermentation was allowed to continue. 80 hours after inoculation, the final results were: 1-lactic acid: 0.06 g/l; total lactic acid: not detected; acetic acid: 10.2 g/l; propionic acid: 22.4 g/l; succinic acid: 5 g/l. Propionic, acetic, and 1-lactic acids and absorbance (600 nm) are plotted against time in FIG. 4. Typically the total lactic acid concentration was approximately double that of 1-lactic acid, due to racemization of the 1-lactic acid in the medium.

EXAMPLE 8

Fed-batch Fermentation With Filter Sterilized Medium

Concentrated medium was prepared in a 750 ml thick-wall bottle and contained deionized water: 120 g; Tastone 154: 31 g; corn steep liquor (National Starch and Chemical Corporation, Bridgewater, N.J.): 77.5 g; $MgSO_4 \cdot 7H_2O$: 0.62 g; ammonium sulfate: 3.72 g; $CaCl_2 \cdot 2H_2O$: 0.775 g. The pH was adjusted to 7.1 using NaOH, and then the concentrate was purged with $CO_2$ for 20 minutes until the pH had been readjusted back to neutrality. The bottle was quickly sealed (using a butyl rubber septum, steel cap, and crimping tool), and was autoclaved for 30 minutes at 121° C. Six liters of 34.1 g/l 88% 1-lactic acid in deionized water were prepared in a glass carboy and sparged with nitrogen. The pH was adjusted to 7.2 with NaOH, then the contents of the carboy were transferred to a 20-liter fermentor equipped with temperature and agitation control.

A 24 gram amount of $Na_2CO_3$ was added, then the fermentor contents were sparged with $CO_2$ until the pH returned to 7.0. The contents of the fermentor were then heated to 82° C. and held at that temperature for 30 minutes in order to reduce the $O_2$ concentration. The contents were cooled to 39° C. while maintaining a pressure of 1 psig with $CO_2$. 13 liters of 34.1 g/l 8% 1-lactic acid in deionized water were purged with nitrogen, pH-adjusted with sodium hydroxide and sodium carbonate, sparged with $CO_2$, and heat treated using the same procedure.

A 14-liter glass fermentor was partially filled with water, and sterilized in the autoclave at 121° C. for 45 minutes. Upon removal from the autoclave, a continuous $CO_2$ purge of 150 cc/min was begun (through sterile glass wool), and the water was removed aseptically. The fermentor medium was prepared by aseptically adding: 1) 2.5 liters of the heat-treated sodium lactate solution (pumped into the fermentor through a 0.2 μm sterilizing filter), 2) 2.5 ml of autoclaved 0.1% resazurin (in water), 3) 32.6 ml of the concentrated medium (above), 4) 16.7 ml of vitamin concentrate (prepared as in Example 7 and added through a sterile 0.45 μm filter), and 5) 8.3 ml of a 15% solution of $Na_2S \cdot 9H_2O$ (added through a sterile 0.45 μm filter).

A second 14-liter glass fermentor containing water was sterilized in place for 30 minutes at 121° C. Upon cooling, vacuum was broken with a continuous $CO_2$ sparge. The water was aseptically removed from the fermentor, and the 13 liters of heat treated sodium lactate solution were pumped into the fermentor through a 0.2 μm sterilizing filter. Afterward the remainder of the sterile concentrated medium prepared above was aseptically transferred to the fermentor, and 13 ml of autoclaved 0.1% resazurin (in water) were injected into the fermentor. 86.7 ml of vitamin concentrate (prepared as in Example 7) were then injected into the fermentor through a sterile 0.45 μm filter.

The first fermentor, containing 2.5 l of medium, was inoculated with 100 ml of an 18-hr culture of S. ruminantium. Fermentation conditions were the same as in Example 7. Twelve hours after inoculation, the fermentor contained l-lactic, total lactic, acetic, propionic, and succinic acid concentrations of 4.8, 10, 2.7, 6.9, and 0.8 g/l respectively. These determinations were made as described in Example 7. 30 minutes later 43.3 g of 15% $Na_2S \cdot 9H_2O$ (in water) were injected into the 13 liters of sterile medium through a 0.45 μm sterile filter, and transfer as a feed to the fermentation was begun. The medium was transferred through sterile tubing using a peristaltic pump at a rate of 2.25 l/h. Transfer was stopped after four hours, at which time 9.0 liters had been transferred, and the fermentation was allowed to continue. 27 hours after inoculation, the fermentor contained l-lactic, total lactic, acetic, propionic, and succinic acid concentrations of 2.0, 4.4, 4.3, 9.4, and 2.4 g/l respectively. In order to prevent the lactic acid from being depleted, sterile sodium lactate solution (prepared as described in Example 7 using 268.1 g of 88% l-lactic acid) was aseptically transferred to the fermentor 90 minutes later, and the fermentation was allowed to continue. 53 hours after inoculation, l-lactic, total lactic, acetic, propionic, and succinic acid concentrations were 0.38, not detected, 8.5, 18.8, and 5.2 g/l respectively. In order for the fermentation to continue, sterile sodium lactate was prepared as described above, but with 300 g of 88% l-lactic acid. Feed of this sterile sodium lactate solution to the fermentor was begun 54 hours after inoculation, at a rate of 10.1 g/h, and was maintained for 27 hours. Final results, 83 hours after inoculation, were: l-lactic acid: 0.63 g/l; total lactic acid: 1.7 g/l; acetic acid: 10.7 g/l; propionic acid: 22.5 g/l; succinic acid: 6.0 g/l. l-lactic, acetic, and propionic acids and absorbance (600 nm) are shown plotted against time in FIG. 5. As in Example 7, the concentration of total lactic acid was typically double that of l-lactic acid.

EXAMPLE 9

Growth Of *Selenomonas ruminantium* In Continuous Culture

One liter of CSL medium (Table 1) was prepared using deionized water, but with 34.1 g/l of l-lactic acid (88%, USP heat stable; Purac, Inc., Arlington Heights, Ill.), 5.0 g/l CSL (National Starch and Chemical Corp., Bridgewater, N.J.), 0.1 mg/l PABA, and 1.0 mg/l biotin. The medium was transferred to a 2-liter fermentor, 4.0 g/l $Na_2CO_3$ were added (which increased the pH to about 10), then $CO_2$ was sparged through the medium until pH dropped to about 7.0. The fermentor was sterilized in place at 121° C. for 30 minutes. Upon cooldown, vacuum was broken by introduction of a $CO_2$ sparge (through a sterilizing filter), which was maintained at a rate of 15-45 cc/min throughout the remainder of the fermentation. 3.3 ml of a heat sterilized 15% aqueous solution of $Na_2S \cdot 9H_2O$ were added, then the fermentor was inoculated with 40 ml of a 26 hour culture of S. ruminantium. Temperature and agitation were maintained at 39° C. and 100 RPM respectively, and pressure was atmospheric.

10.0 liters of medium were prepared in a 14-l glass fermentor in the manner described above, to be used as feed for continuous culture. 4.0 g/l of $Na_2CO_3$ were added and then $CO_2$ was sparged through the medium until the pH dropped to about 7.0. The fermentor was autoclaved at 121° C. for 45 minutes. Upon cooling, a $CO_2$ sparge (through sterile glass wool) was applied and maintained at a rate of 150 cc/min throughout the remainder of the fermentation. $Na_2S \cdot 9H_2O$ was not added until immediately before continuous feeding began (see below). Temperature, agitation, and pressure were maintained at 39° C., 200 RPM, and atmospheric respectively.

When the lactic acid in the 2 liter fermentor was nearly depleted by growth of S. ruminantium, 33.5 ml of a sterile 15% aqueous solution of $Na_2S \cdot 9H_2O$ were added to the 14-l fermentor. A continuous feed of medium from the 14-l to the 2-l fermentor was begun (using a peristaltic pump), and spent broth was removed at the same rate to maintain the volume constant at 1.0 l. Continuous culture was maintained in this manner for 13 days. The following steady state conditions were obtained (with assays performed as described in Example 7):

| | |
|---|---|
| lactic acid | 6.0 g/l |
| lactic acid utilization | 80% |
| propionic acid | 10.8 g/l |
| acetic acid | 5.1 g/l |
| succinic acid | 3.4 g/l |
| absorbance | 5.5 g/l |
| dilution rate | 0.055 /h |
| propionic acid productivity | 0.59 g/l·h |

EXAMPLE 10

Study of Corn Steep Liquors

An experiment was set up to determine if differences in mineral content might affect the ability of corn steep liquors from various sources to produce propionic acid. Each CSL fermentation medium, prepared according to Table 1, heat sterilized, and inoculated with an overnight culture of S. ruminantium, was supplemented with trace minerals at a level of 11.0 ml of an aqueous solution of the minerals (along with 5.5 g/liter of citric acid as a chelating agent) per liter of medium. The solution contained, in g/l: $Na_2MoO_4 \cdot 2H_2O$ 0.025, $FeSO_4 \cdot 7H_2O$ 0.95, $CuSO_4 \cdot 5H_2O$ 0.05, $Na_2SeO_3$ 0.001, $ZnSO_4 \cdot 7H_2O$ 0.39, $MnSO_4 \cdot H_2O$ 0.08, $Na_2CrO_4 \cdot 4H_2O$ 0.005, and $H_3BO_3$ 0.09. While liquid CSL was added as specified in Table 3 at a level of 5 g/l of the medium, spray dried CSL was added at a level of 0.25 g/l. The results (Table 3) showed that mineral supplements did not improve either growth rate or propionic acid yield, when liquid CSL was used, but somewhat improved growth with the spray dried CSL. The results also showed that spray dried CSL produces a lower growth rate than liquid CSL, but similar 48 hour yields of propionic acid (Table 3). Thus, liquid CSL is preferred.

We claim:

1. A process for preparing a salt of propionic acid selected from the group consisting of sodium and calcium salts, comprising fermenting with the bacterium *Selenomonas ruminantium* under conditions of reduced oxygen concentrations an aqueous medium containing lactic acid, carbon dioxide, and a neutralizing agent selected from the group consisting of sodium hydroxide, calcium carbonate, and calcium hydroxide with the same metal ion as the said salt, the said process providing a yield in the said medium of at least 1% of the salt of propionic acid.

2. A process for preparing a salt of propionic acid as claimed in claim 1 in which the medium contains corn steep liquor that is a source of lactic acid.

3. A process for preparing a salt of propionic acid as claimed in claim 1 in which an additional amount of lactic acid is added to the medium, and the amount in the medium is at least 2%.

4. A process for preparing a salt of propionic acid as claimed in claim 3 in which the lactic acid is added to the medium to provide a weight-to volume concentration of 1-3%.

5. A process for preparing a salt of propionic acid as claimed in claim 3 in which the medium contains soy peptone.

6. A process for preparing a salt of propionic acid as claimed in claim 2, in which the cation selected from the said group is sodium.

7. A process for preparing a salt of propionic acid as claimed in claim 1 which includes the step of removing oxygen from the medium by adding an effective amount of a reducing agent.

8. A process for preparing a salt of propionic acid as claimed in claim 7 in which the reducing agent is selected from the group consisting of sodium sulfide and cysteine.

9. A process for preparing a salt of propionic acid as claimed in claim 1, in which the medium also contains at least one vitamin selected from the group consisting of d-biotin, p-aminobenzoic acid, choline, folic acid, inositol, niacin, pantothenic acid, pyridoxine, riboflavin, and thiamine.

10. A process for preparing a salt of propionic acid as claimed in claim 9, in which the medium contains d-biotin and p-aminobenzoic acid.

11. A process for preparing a salt of propionic acid as claimed in claim 8, in which the medium also contains yeast extract.

12. A process for preparing a salt of propionic acid as claimed in claim 1, comprising the steps of preparing an aqueous medium in a fermentor vessel, adding about 3% weight by volume of lactic acid, adding a neutralizing agent selected from the group consisting of sodium hydroxide, calcium carbonate, and calcium hydroxide, and then bubbling carbon dioxide through it, adding an aqueous solution of sodium sulfide, inoculating the medium in the fermentor with $S.$ $ruminantium$, and whenever the initial lactic acid is depleted by the fermentation, adding another 2% lactic acid until a yield of at least 1% is reached.

13. A process for preparing a salt of propionic acid as claimed in claim 1, comprising the steps of preparing an aqueous medium in a fermentor vessel, the medium containing lactic acid and a neutralizing agent selected from the group consisting of sodium hydroxide, calcium carbonate, and calcium hydroxide, sterilizing the medium, bubbling carbon dioxide through it, adding an aqueous solution of sodium sulfide, preparing a similar medium in a separate vessel connected with the fermentor for controlled feed to the fermentor, inoculating the medium in the fermentor with $S.$ $ruminantium$, continuously feeding medium from the feed vessel to the fermentor, continuously removing medium from the fermentor, and isolating the propionic acid salt from the medium.

14. A process for preparing a salt of propionic acid as claimed in claim 13, in which the inoculation is with 3-5% by volume of a 12-36 hour culture of $S.$ $ruminantium$.

15. A process for preparing a salt of propionic acid as claimed in claim 13, in which the feeding of the medium begins when the lactate concentration in the fermentor drops to $<10$ g/l.

16. A process for preparing a salt of propionic acid as claimed in claim 14, which converts 5 moles of lactate into about 3 moles of propionate, about 1.7 moles of acetate, and about 0.4 moles of succinate.

17. A fermentation product prepared by the process of claim 1, mixture of up to 5% of a lactate selected from the group consisting of sodium lactate and calcium lactate, carbon dioxide, sufficient $Na_2S$ or other suitable reducing agent to eliminate all but traces of oxygen, and the fermentation products propionate, acetate and succinate salts, the content of propionic acid (as sodium propionate) being at least 1%.

18. A fermentation product mixture comprising lactic acid as claimed in claim 17, containing lactic acid, $<0.1$ g/l; acetic acid, 7-11 g/l; propionic acid, 20-24 g/l; succinic acid, 4-5 g/l.

19. A fermentation product mixture as claimed in claim 17, containing propionic acid, acetic acid and succinic acid in a ratio of about 7.5:4.2:1.0, respectively.

* * * * *

UNITED STATES PATENT AND TRADEMARK OFFICE
CERTIFICATE OF CORRECTION

| | | |
|---|---|---|
| PATENT NO. : | 5,137,736 | Page 1 of 3 |
| DATED : | August 11, 1992 | |
| INVENTOR(S) : | David C. Eaton et al | |

Figure 4:
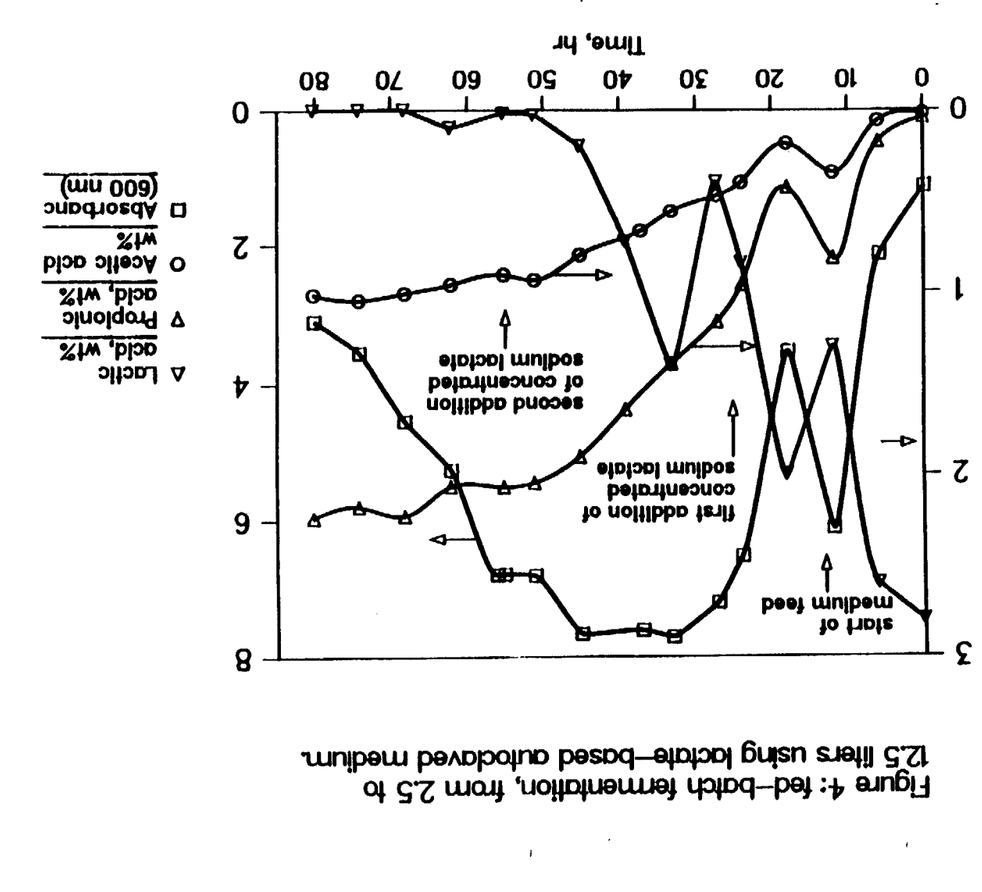
Figure 5:
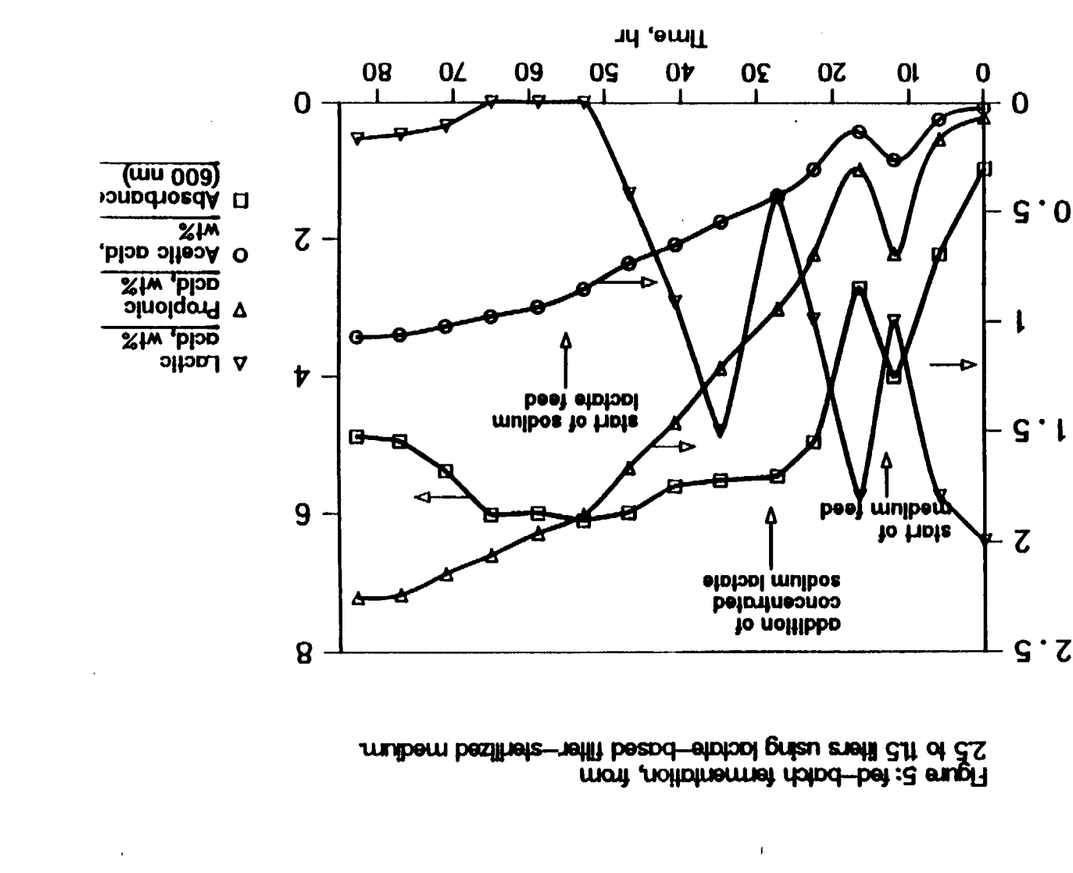

It is certified that error appears in the above-identified patent and that said Letters Patent is hereby corrected as shown below:

In the drawings: Figs. 4 and 5, as shown on the attached pages, should be added.

Signed and Sealed this

Sixteenth Day of May, 1995

Attest:

BRUCE LEHMAN

*Attesting Officer*  *Commissioner of Patents and Trademarks*

Figure 5: fed-batch fermentation, from 2.5 to 11.5 liters using lactate-based filter-sterilized medium.

Figure 4: fed-batch fermentation, from 2.5 to 12.5 liters using lactate-based autoclaved medium.

△ Lactic acid, wt%
▽ Propionic acid, wt%
○ Acetic acid wt%
□ Absorbance (600 nm)